United States Patent
Ko et al.

(10) Patent No.: US 11,426,598 B2
(45) Date of Patent: Aug. 30, 2022

(54) REUSABLE ADHESIVE PAD WITH EMBEDDED MAGNETS

(71) Applicants: Wen-Shen Ko, Taipei (TW); Chih-Han Ko, Taipei (TW); Wang-Hsiang Ko, Taipei (TW); Wei Chen, Taichung (TW)

(72) Inventors: Wen-Shen Ko, Taipei (TW); Chih-Han Ko, Taipei (TW); Wang-Hsiang Ko, Taipei (TW); Wei Chen, Taichung (TW)

(73) Assignees: Wen-Shen Ko, Taipei (TW); Chih-Han Ko, Taipei (TW); Wang-Hsiang Ko, Taipei (TW)

(*) Notice: Subject to any disclaimer, the term of this patent is extended or adjusted under 35 U.S.C. 154(b) by 575 days.

(21) Appl. No.: 16/433,345

(22) Filed: Jun. 6, 2019

(65) Prior Publication Data
US 2019/0374788 A1  Dec. 12, 2019

(30) Foreign Application Priority Data
Jun. 7, 2018  (TW) ................................ 107207630

(51) Int. Cl.
*A61N 2/00* (2006.01)
*A61N 2/06* (2006.01)
*A61F 13/02* (2006.01)

(52) U.S. Cl.
CPC .............. *A61N 2/008* (2013.01); *A61F 13/02* (2013.01); *A61N 2/06* (2013.01)

(58) Field of Classification Search
CPC ........... A61N 2/008; A61N 2/06; A61F 13/02; A61F 13/0206; A61F 13/00051
(Continued)

(56) References Cited

U.S. PATENT DOCUMENTS 4,391,270 A * 7/1983 Uragami .................. A61N 2/06
600/15
4,480,596 A * 11/1984 Shumiyashu ............ A61N 2/06
600/15
(Continued)

OTHER PUBLICATIONS

Park TH, Rah DK. Successful eradication of helical rim keloids with surgical excision followed by pressure therapy using a combination of magnets and silicone gel sheeting. Int Wound J. Apr. 2017;14(2):302-306. doi: 10.1111/iwj.12547. Epub Nov. 23, 2015. PMID: 26593457; PMCID: PMC7949688. (Year: 2017).*

*Primary Examiner* — Sunita Reddy
(74) *Attorney, Agent, or Firm* — Muncy, Geissler, Olds & Lowe, P.C.

(57) ABSTRACT

A reusable adhesive pad with embedded magnets consists of a layer of fibrous cloth with elasticity, a layer of silicone gel padding, and permanent magnets. The fibrous cloth with elasticity is made from fiber materials with a stretchable characteristic. The silicone gel padding is spread out fully and glued on one surface of the fibrous cloth with elasticity. In addition, the silicone gel padding is provided with holes that the permanent magnets with cylindrical or conical outers can be filled in and glued to the adhesive surface of the fibrous cloth with elasticity. Since the other sides of the permanent magnets protrude outwards the surface of the silicone gel padding, applying the invention to the human skin can perform the acupuncture and moxibustion treatment and the magneto-therapy to lessen painful discomfort.

4 Claims, 5 Drawing Sheets

(58) Field of Classification Search
USPC .......................................................... 600/9–15
See application file for complete search history.

(56) References Cited

U.S. PATENT DOCUMENTS

| | | | | |
|---|---|---|---|---|
| 5,246,456 | A * | 9/1993 | Wilkinson | A61F 5/0086 604/909 |
| 5,720,046 | A * | 2/1998 | Lopez | A42B 1/24 2/159 |
| 5,792,176 | A * | 8/1998 | Chang | A61H 39/04 128/898 |
| 6,284,941 | B1 * | 9/2001 | Cox | A61K 9/7084 602/41 |
| 6,344,021 | B1 * | 2/2002 | Juster | A61N 2/06 600/15 |
| 6,963,019 | B2 * | 11/2005 | Binder | A61F 13/0273 602/48 |
| 2004/0167373 | A1 * | 8/2004 | Xie | A61N 2/002 600/9 |
| 2005/0113732 | A1 * | 5/2005 | Lawry | A61F 13/0203 602/48 |
| 2005/0165445 | A1 * | 7/2005 | Buckman | A61F 13/00 606/213 |
| 2020/0129412 | A1 * | 4/2020 | Jager | A61K 9/7007 |

* cited by examiner

REUSABLE ADHESIVE PAD WITH EMBEDDED MAGNETS

BACKGROUND OF THE INVENTION

(a) Field of the Invention

The present invention relates to a reusable adhesive pad with embedded magnets, and more particularly to a structure of a patch that is able to be pasted to the human skin for more than one time to relieve painful discomfort.

(b) Description of the Prior Art

When a person has painful discomfort caused by poor circulation of blood, hard use of joints and muscles, or stiff aching muscles, the person usually pastes medicinal patches with pain relief ingredients or Chinese herbal medicine over the affected areas. However, the way of treatment described above has some shortcomings including short medicinal effectiveness, allergy symptoms on the skin, and patches being non-reusable.

Another existing way of treatment to lessen painful discomfort is to apply a so-called "magnetic adhesive patch" to a meridian acupuncture point of the person. The magnetic adhesive patch is normally made of a small round of permanent magnet and a small piece of circular shaped patch coated with glue substances on one side of the patch. The application of the magnetic adhesive patch is to paste a permanent magnet on the skin of a certain meridian acupuncture point of the human body to perform the theory of acupuncture and moxibustion in order to heal aches and pains. Since the permanent magnet is directly adhered on the meridian acupuncture point to improve the qi (vital energy) and the blood circulation, the effectiveness of the treatment can be relatively long. However, the coated glue substances on the patch will be easily polluted by scurf, fur, oil and perspiration of the human skin, making the magnetic adhesive patch unfit for reuse. Moreover, peeling off the magnetic adhesive patch may cause skin irritation and leave remnants of the glue substances on the skin.

Hence, it can be seen that the aforementioned products of the prior art still have many shortcomings, and in reality are not good designs and in need of urgent improvement.

SUMMARY OF THE INVENTION

The main objective of the present invention is to provide a reusable adhesive pad with embedded magnets which can be easily used and reused to perform the magneto-therapy on a human body to heal aches and pains. In other words, the invention is able to solve the problems caused by scurf, fur, oil and perspiration of a human body as well as troubles of the skin irritation and the remnants of glue substances on the skin. A gel padding made from medical grade of silicone and a fibrous cloth with elasticity are used to achieve the objective.

Accordingly, the reusable adhesive pad with embedded magnets of the present invention comprises a layer of fibrous cloth with elasticity, a layer of silicone gel padding and permanent magnets with cylindrical or conical outers. The layer of fibrous cloth with elasticity is made from fiber materials with a stretchable characteristic. The layer of silicone gel padding, made from 100% medical grade silicone, is spread out fully and glued on one side of the fibrous cloth with elasticity to form the size and the shape of the invention. The 100% medical grade silicone is hypoallergenic, washable, durable, reusable and adhesive to the human skin. The silicone material also provides cushions to absorb force and pressure. In addition, the silicone gel padding has holes, by drilling, punching or moulding, so that the permanent magnets with cylindrical or conical outers are filled in the holes and glued to the fibrous cloth of elasticity. As a result, one side of each of the permanent magnets with cylindrical or conical outers is fixed to the glued side of the fibrous cloth with elasticity, while the other side protrudes outwards through the surface of the silicone gel padding.

When a person has painful discomfort caused by poor circulation of blood, hard use of joints and muscles, or stiff aching muscles, the invented reusable adhesive pad with embedded magnets can be applied to the skin of the affected areas or the corresponding meridian acupuncture spots to perform the magneto-therapy through the permanent magnets with cylindrical or conical outers. Because of the 100% medical grade silicone, the layer of silicone gel padding is reusable and re-adhesive on anywhere of the human skin. The layer of fibrous cloth with elasticity works as a shield to relieve friction and pressure from the garments and as a pattern to form the size and the shape of the silicone gel padding.

To enable a further understanding of the objectives and the technological methods of the invention herein, a brief description of the drawings is provided below followed by a detailed description of the preferred embodiments.

DETAILED DESCRIPTION OF THE PREFERRED EMBODIMENTS

Figure 1:
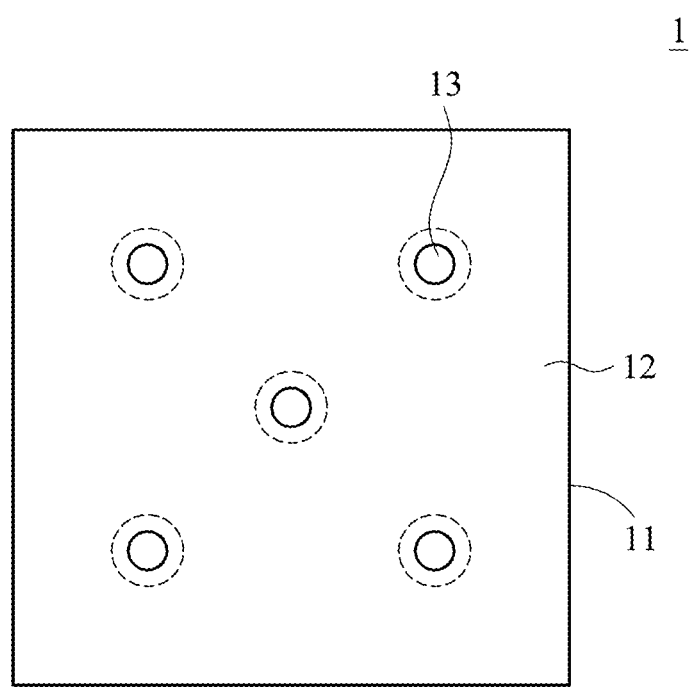
FIG. 1 is a top schematic view of a reusable adhesive pad with embedded magnets of the present invention.
Figure 2:
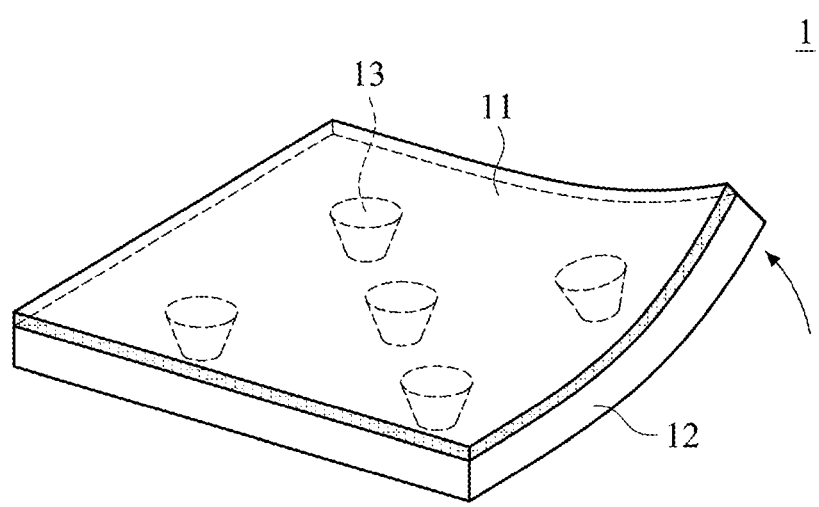
FIG. 2 is a schematic view of an application of the reusable adhesive pad with embedded magnets of the present invention.
Figure 3:
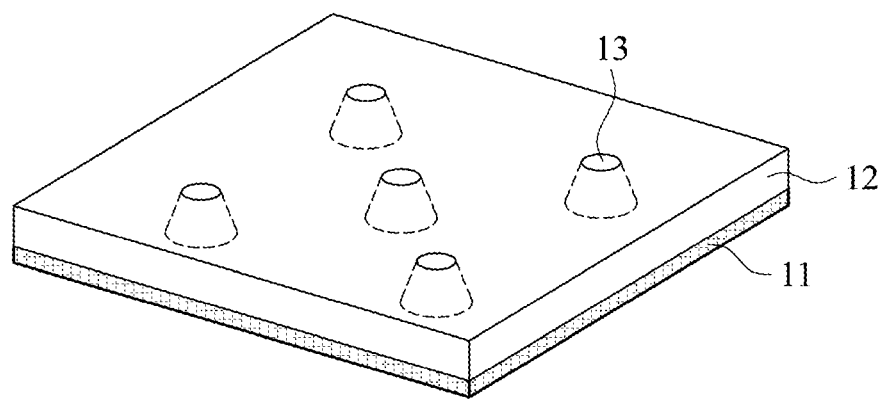
FIG. 3 is a three-dimensional schematic view of the cross section of the reusable adhesive pad with embedded magnets of the present invention.
Figure 4:
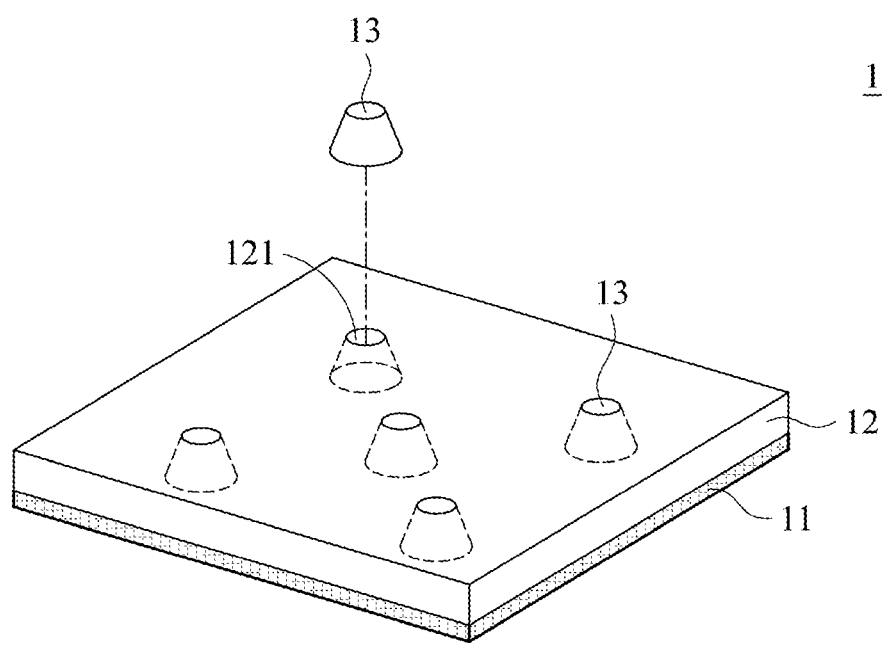
FIG. 4 is a three-dimensional schematic view with a magnet assembly to the reusable adhesive pad with embedded magnets of the present invention.

The present invention relates to a reusable adhesive pad with embedded magnets, and FIGS. 1, 2, 3, 4 show the structure of the reusable adhesive pad with embedded magnets 1, primarily comprising a layer of fibrous cloth with elasticity 11, a layer of silicone gel padding 12, and permanent magnets with conical or cylindrical outers 13.

The layer of fibrous cloth with elasticity 11 is made from fiber materials with a stretchable characteristic, including textiles and non-woven fabric.

The layer of silicone gel padding 12 is spread out flat and glued on one surface of the fibrous cloth with elasticity 11 to have structural support and to form a pattern for the size and the shape of the reusable adhesive pad with embedded magnets 1. The layer of silicone gel padding 12 is provided with holes 121.

The permanent magnets with cylindrical or conical outers 13 are respectively filled in the holes 121, wherein one side of each of the permanent magnets is glued and fixed to the adhesive surface of the fibrous cloth with elasticity 11, and the other side protrudes outwards through the respective hole 121 and the surface of the silicone gel padding 12. The permanent magnets 13 can contact the skin.

According to the assembly of the components described above, the reusable adhesive pad with embedded magnets 1 can be applied to a certain meridian acupuncture point on a human body. Since the permanent magnets 13 protrude outwards from the holes 121 and touch the skin, the permanent magnets 13 will produce magnetic fields to stimulate the meridian acupuncture point, similar to the treatment of acupuncture and moxibustion, to heal aches and pains. In addition, the reusable adhesive pad with embedded magnets 1 can be adhered to an affected area of stiff aching muscles and joints to perform magneto-therapy to improve qi (vital energy) and poor blood circulation in the human body and lessen painful discomfort.

Furthermore, the silicone gel padding 12 is made from 100% medical grade silicone with characteristics of hypoallergenic, washable, durable, reusable and adhesive to the human skin, the reusable adhesive pad with embedded magnets 1 can be pasted onto the human skin, peeled off and re-pasted again.

Referring again to FIGS. 1, 2, 3, 4, clean water can be used to wash off foreign substances such as scurf, fur, oil and perspiration of the human skin on the silicone gel padding 12 after usage to restore the adhesiveness of the reusable adhesive pad with embedded magnets 1 to the human skin.

Referring again to FIGS. 1, 2, 3, 4, the layer of fibrous cloth with elasticity 11 provides a shield to protect the human skin from the friction and pressure from the garments.

Referring again to FIGS. 1, 2, 3, 4, the layer of fibrous cloth with elasticity 11 and the layer of silicone gel padding 12 can be trimmed to any geometric shape, including circular, elliptical, square, rectangular, rhomboidal or triangular.

Figure 5:
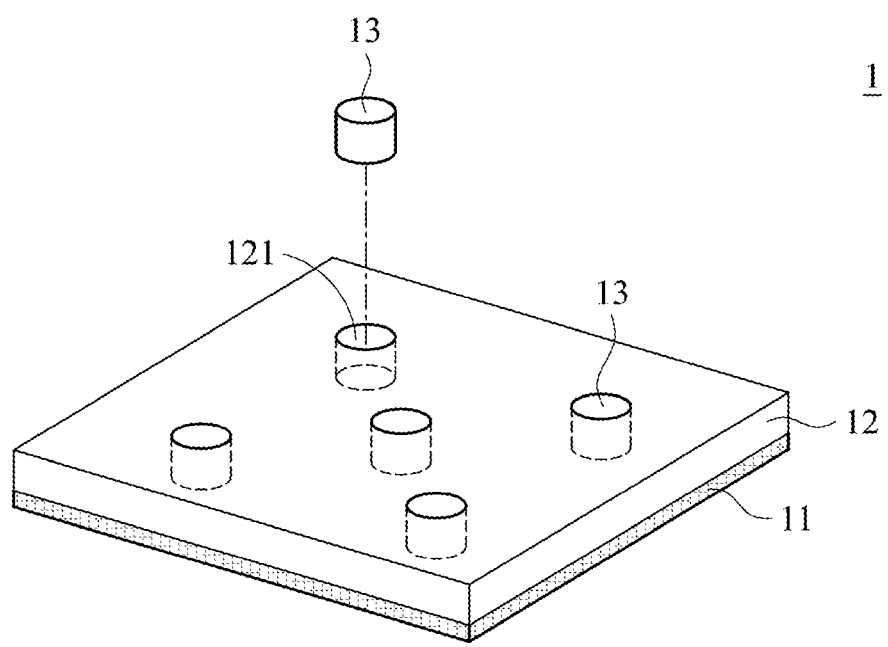
FIG. 5 is a three-dimensional schematic view of another embodiment of the reusable adhesive pad with embedded magnets of the present invention.

Referring again to FIGS. 1, 2, 3, 4, 5, the outers of the permanent magnets 13 can be conical and cylindrical.

Accordingly, the reusable adhesive pad with embedded magnets 1 disclosed in the present invention has the following features and advantages:

1. The layer of silicone gel padding 12 is used to enable the reusable adhesive pad with embedded magnets 1 to adhere to the human skin.

2. The layer of fibrous cloth with elasticity 11 is used to provide a stretching force to apply the reusable adhesive pad with embedded magnets 1 to anywhere on the human skin, and is also used to shield friction and pressure between the reusable adhesive pad with embedded magnets 1 and garments.

3. The permanent magnets 13 are used to provide magnetic fields needed to perform acupuncture and moxibustion as well as magneto-therapy on a human body.

4. The layer of silicone gel padding 12 is provided with holes 121, used to hold the permanent magnets 13 and to secure their contact with the human skin.

5. The layer of fibrous cloth with elasticity 11 provides the adhesion to fix the layer of silicone gel padding 12 and the permanent magnets 13.

6. When the reusable adhesive pad with embedded magnets 1 is pasted and lightly pressed onto the human skin, a perpendicular pressure will be acted to expel air between the silicone gel padding 12 and the human skin. The adhesiveness of the silicone materials, the atmospheric pressure and the frictional force enable the reusable adhesive pad with embedded magnets 1 to adhere to the human skin firmly.

7. When an edge of the reusable adhesive pad with embedded magnets 1 is separated from the human skin, an air layer will be produced between the layer of silicone gel padding 12 and the human skin to free the atmospheric pressure such that the reusable adhesive pad with embedded magnets 1 can be easily peeled off and removed from the skin.

In conclusion, the reusable adhesive pad with embedded magnets of the present invention has a hitherto unknown innovative structure not found in the prior art. Moreover, no similar products have been seen in any publication or in the market. The present invention is provided with undoubted originality.

It is of course to be understood that the embodiments described herein are merely illustrative of the principles of the invention and that a wide variety of modifications thereto may be effected by persons skilled in the art without departing from the spirit and scope of the invention as set forth in the following claims.

What is claimed is:

1. A reusable adhesive magnetic therapy pad with embedded magnets, comprising:
   a layer of fibrous elastic cloth;
   a layer of silicone gel padding configured to adhere to a human skin surface, wherein the layer of silicone gel padding is 100% medical grade silicone,
   wherein the layer of silicone gel padding is spread out and glued to a surface of the fibrous elastic cloth, and wherein the layer of silicone gel padding is further provided with a plurality of holes; and
   a plurality of frustoconical-shaped permanent magnets positioned within the plurality of holes in the layer of silicone gel padding and glued to the surface of the fibrous elastic cloth, wherein each magnet includes an embedded portion positioned inside one of the plurality of holes and a protruding portion protruding outside that hole, wherein the protruding portion of each magnet is narrower than the embedded portion of that magnet, and wherein the protruding portion of each magnet is configured to contact the human skin surface for rendering magnetic therapy.

2. The reusable adhesive pad with embedded magnets according to claim 1, wherein the materials of the fibrous cloth are textiles or non-woven fabric patch.

3. The reusable adhesive pad with embedded magnets according to claim 1, wherein the layer of fibrous elastic cloth and the layer of silicone gel padding is trimmed to any geometric shape.

4. The reusable adhesive pad with embedded magnets according to claim 3, wherein the geometric shape is circular, elliptical, square, rectangular, rhombic or triangular.

* * * * *